(12) United States Patent
Okawa et al.

(10) Patent No.: US 7,864,310 B2
(45) Date of Patent: Jan. 4, 2011

(54) SURFACE INSPECTION METHOD AND SURFACE INSPECTION APPARATUS

(75) Inventors: Takashi Okawa, Fujioka (JP); Kenji Mitomo, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/576,580

(22) Filed: Oct. 9, 2009

(65) Prior Publication Data
US 2010/0026996 A1 Feb. 4, 2010

Related U.S. Application Data

(63) Continuation of application No. 11/822,469, filed on Jul. 6, 2007, now Pat. No. 7,616,299.

(30) Foreign Application Priority Data

Jul. 7, 2006 (JP) .............................. 2006-187344

(51) Int. Cl.
*G01N 21/00* (2006.01)
(52) U.S. Cl. ................................. 356/237.1; 356/237.4
(58) Field of Classification Search ... 356/237.1–241.6, 356/242.1–243.8, 426–431, 600–640
See application file for complete search history.

(56) References Cited

U.S. PATENT DOCUMENTS

| 4,410,278 | A | * | 10/1983 | Makihira et al. ............. 356/445 |
| 4,598,997 | A | | 7/1986 | Steigmeier et al. |
| 4,672,196 | A | | 6/1987 | Canino |
| 4,794,264 | A | | 12/1988 | Quackenbos et al. |
| 5,144,495 | A | | 9/1992 | Merton et al. |
| 5,307,154 | A | * | 4/1994 | Naemura et al. ............ 356/400 |
| 5,903,342 | A | * | 5/1999 | Yatsugake et al. ......... 356/237.4 |
| 5,909,276 | A | | 6/1999 | Kinney et al. |
| 6,011,762 | A | | 1/2000 | Watanabe et al. |
| 6,104,481 | A | | 8/2000 | Sekine et al. |
| 6,201,601 | B1 | * | 3/2001 | Vaez-Iravani et al. .... 356/237.4 |
| 6,271,916 | B1 | | 8/2001 | Marxer et al. |
| 6,432,800 | B2 | | 8/2002 | Park |
| 6,798,504 | B2 | * | 9/2004 | Sato et al. ................. 356/237.2 |
| 7,120,228 | B2 | * | 10/2006 | Yokhin et al. .................. 378/90 |
| 7,203,155 | B2 | | 4/2007 | Nakamura et al. |
| 7,417,244 | B2 | * | 8/2008 | Ishimaru et al. ........ 250/559.46 |
| 7,426,023 | B2 | * | 9/2008 | Ohshima et al. ......... 356/237.2 |
| 7,643,139 | B2 | * | 1/2010 | Ohshima et al. ......... 356/237.4 |
| 2002/0098528 | A1 | | 7/2002 | Gordon et al. |
| 2003/0059803 | A1 | | 3/2003 | Werner et al. |
| 2006/0065625 | A1 | * | 3/2006 | Abdulhalim et al. .......... 216/59 |

FOREIGN PATENT DOCUMENTS

JP 9-304289 11/1997

* cited by examiner

*Primary Examiner*—Gregory J Toatley
*Assistant Examiner*—Jarreas C Underwood
(74) *Attorney, Agent, or Firm*—McDermott Will & Emery LLP

(57) ABSTRACT

When measuring an edge region, a photo detector with an angle not influenced by the diffracted light, the diffracted light causing noise, is selected to thereby allow for inspection that minimizes the sensitivity reduction. This allows for the management of foreign matters in the outer peripheral portion, which conventionally could not be measured, and this also eliminates the oversight of critical defects on the wafer, thus leading to reduction of failures of IC.

5 Claims, 3 Drawing Sheets

SURFACE INSPECTION METHOD AND SURFACE INSPECTION APPARATUS

This application is a Continuation of U.S. patent application Ser. No. 11/822,469, filed on Jul. 6, 2007, now U.S. Pat. No. 7,616,299, claiming priority of Japanese Application No. 2006-187344, filed on Jul. 7, 2006, the entire contents of each of which are hereby incorporated by reference.

BACKGROUND OF THE INVENTION

The present invention relates to a surface inspection method and surface inspection apparatus of an object to be inspected.

Examples of the surface inspection method and surface inspection apparatus of an object to be inspected include a method and apparatus for inspecting the surface of a wafer as described in JP-A-9-304289, for example. A laser beam outputted from a laser beam source is focused into a laser spot Sp (hereinafter, referred to as a spot Sp) by a lens system and is projected approximately perpendicularly or obliquely onto the surface of a wafer, and the surface of a wafer is spirally scanned corresponding to a displacement of the wafer, and as a result the whole surface of the wafer is scanned. When a foreign matter e is present on the surface of a wafer, a scattered light Se is generated in a wide range of angles (directions). A part thereof is condensed with a condenser lens and is received by a plurality of photomultiplier tubes (hereinafter, referred to as PMT) serving as photoelectric converters. Here, the beam incident upon the plurality of PMTs is converted into an electric signal and the converted electric signal (received light signal) is subjected to data processing. As a result of the data processing, the data of the foreign matter indicative of the number, size, and position of the foreign matter e is generated, and the conditions of the foreign matters are displayed in a map form on a printer (not shown) or on a display (not shown).

SUMMARY OF THE INVENTION

In the conventional art described above, due to the influence of diffracted light from a specified region (for example, edge region) of an object to be inspected, a noise component increases and a signal from the foreign matter is buried, so that it is difficult to detect defects of the region concerned.

An object of the present invention is to provide an inspection method and inspection apparatus for preventing the influence of a noise component that generates from an object to be inspected when inspecting the surface of the object to be inspected with a beam.

According to an aspect of the present invention, in a method including the steps of: emitting light onto the surface of an object to be inspected; rotating the object to be inspected; and receiving the light from the surface of the object and thereby inspecting, the amount of the received light is varied when a specified region of the object to be inspected is irradiated with the irradiated light.

According to another aspect of the present invention, the specified region is an edge region of the object to be inspected.

According to yet another aspect of the present invention, in order to vary the amount of the received light, the amount of light to be irradiated is varied and/or the light receiving sensitivity is varied.

According to yet another aspect of the present invention, in order to vary the amount of the received light, the light is received from the direction except the direction of receiving the diffracted light from the edge region of the object to be inspected.

According to yet another aspect of the present invention, in order to vary the amount of the received light, the light is received so that the diffracted light from the edge region of the object to be inspected may decrease.

According to yet another aspect of the present invention, the above-described method includes a light projecting optical system that irradiates the light approximately perpendicularly from above the object to be inspected and/or a light projecting optical system that irradiates the light from the oblique direction of the object to be inspected, and the method further includes a plurality of photo detectors for the light receiving, wherein a photo detector with an angle less likely to be influenced by the diffracted light is selected among the plurality of photo detectors.

According to yet another aspect of the present invention, the light is a laser beam.

According to yet another aspect of the present invention, the object to be inspected is a semiconductor wafer or an insulator wafer.

According to yet another aspect of the present invention, a surface inspection apparatus includes: a light receiving system including a plurality of photo detectors; a light projecting optical system that irradiates light to the surface of an object to be inspected; and a means that identifies a foreign matter by computing signals that the plurality of photo detectors detect via the irradiation of light from the light projecting optical system, and selects at least one of the plurality of photo detectors depending on the position of the light on the object to be inspected.

According to yet another aspect of the present invention, the light receiving system includes a low angle light receiving system having an elevation angle equal to or less than 30 degrees with reference to the surface of an object to be inspected, and a high angle light receiving system having an elevation angle greater than that of the low angle light receiving system, and the light projecting optical system further includes a first light projecting optical system that irradiates a laser beam approximately perpendicularly from above the object to be inspected, and a second light projecting optical system that irradiates a polarized laser beam from the oblique direction of the object to be inspected, wherein defects and foreign matters are discriminated by computing signals that the low angle light receiving system and the high angle light receiving system detect via the irradiation of a laser beam from the first light projecting optical system, and the foreign matter is identified based on a signal that the low angle light receiving system detects via the irradiation of a polarized laser beam from the second light projecting optical system.

According to yet another aspect of the present invention, the surface inspection apparatus further includes an optical system switching mechanism that switches between scanning with the laser beam of the first light projecting optical system and scanning with the second light projecting optical system. According to yet another aspect of the present invention, the surface inspection apparatus further includes a detector for detecting the position of the light on the object to be inspected, wherein the plurality of photo detectors include a photo detector disposed at an angle not influenced by the diffracted light from the edge region of the object to be inspected, and the apparatus further includes a data processing unit that controls the selection of a detector among the plurality of photo detectors in response to the output of the detector.

According to the present invention, it is possible to provide an inspection method and inspection apparatus that prevent the influence of a noise component when inspecting the surface of an object to be inspected via a beam, the noise component generating from the object to be inspected.

Other objects, features and advantages of the invention will become apparent from the following description of the embodiments of the invention taken in conjunction with the accompanying drawings.

BRIEF DESCRIPTION OF THE DRAWINGS

FIGS. 1A-1C are conceptual diagrams showing a semiconductor wafer as an object to be inspected and the intensity of diffracted light from an edge region of the wafer, wherein FIG. 1A shows a top view of the diffracted light at the edge region of the wafer, FIG. 1B shows a side view of the diffracted light at the edge region of the wafer, and FIG. 1C shows a state of the scattered light from a foreign matter, respectively.

FIGS. 2A-2C are simple configuration diagrams of a detection optical system of an inspection apparatus, wherein FIG. 2A shows a top view of the arrangement of photo detectors, FIG. 2B shows a simple side view of the configuration of the optical system, and FIG. 2C shows a detailed diagram of the photo detector, respectively.

DETAILED DESCRIPTION OF THE EMBODIMENT

Figure 1A:
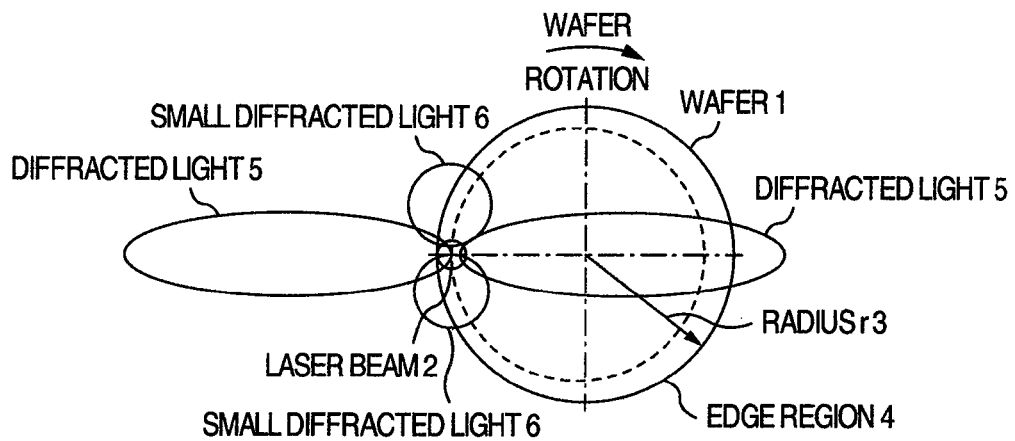

The surface inspection method and surface inspection apparatus of the present invention can be applicable to the objects to be inspected, such as a semiconductor wafer, a wafer-shaped object, an insulator wafers (e.g., a sapphire glass wafer, a silica glass wafer, and the like). As an example, an embodiment applied to the surface inspection of a semiconductor wafer is described next.

A silicon wafer serving as the base material for semiconductor ICs is manufactured from a highly purified polycrystalline silicon. The silicon wafer is manufactured by preparing a single-crystal silicon ingot via a CZ method, and slicing this into thin plates, and polishing the surface and outer peripheral edge of the sliced thin plate to a mirror surface, and then washing foreign matters sticking to the surface thereof.

During these manufacture processes, a foreign matter or a crack may occur in the outer peripheral edge of a wafer. Defects, such as a foreign matter and a scratch in the outer peripheral edge of a wafer, are most likely to become critical defects especially in a large sized wafer (300 mm), and thus there is a need for the surface inspection.

However, in the wafer surface inspection apparatus of the conventional art, a phenomenon, which makes it difficult to detect these foreign matters and defects, occurs because the surface conditions differ between in the surface of a wafer and in the outer peripheral edge (edge region) thereof.

In the above-described conventional art, the influence of diffracted light from the edge region of an object to be inspected increases as the noise component of a detection signal, and the signal of a foreign matter or defect is buried into this noise component, thus making the defect detection of the edge region difficult. An object of this embodiment is to provide an inspection method and inspection apparatus that prevent the influence of the noise component when inspecting the surface of an object to be inspected via a beam, the noise component generating from the object to be inspected. Specifically, it is an object to provide an inspection method and inspection apparatus allowing for inspection of the edge region by suppressing a decrease in the inspection sensitivity in the edge region of an object to be inspected.

A wafer surface inspection apparatus of this embodiment inspects from the central portion to peripheral portion with the same sensitivity in the surface of a wafer. Accordingly, by excluding a region, in which the noise signal increases due to the influence of diffracted light from the peripheral portion of a wafer, as a non-inspection region from the inspection region, it is possible to avoid the influence of noise. However, due to the exclusion from the inspection region as described above, it is impossible to obtain information on the foreign matters and defects. Then, in the present invention, by controlling the position of irradiation light approximately constant and by linearly moving the wafer in an approximately constant direction while rotating the wafer about the approximately center of the wafer surface, the feature that the diffracted light from the wafer edge region is always irradiated to approximately the same direction (orientation) is exploited, and a photo detector is disposed also at an angle (direction) not influenced by the diffracted light from the wafer edge region, thereby allowing for the selection of at least one or more photo detectors among a plurality of photo detectors or the selection of the inspection region depending on the inspection region (position). Moreover, the control of the selection of one or more electric signals, the conversion processing of each electric signal, the calculation processing between the electric signals, and the like, are also allowed depending on the desired information on the foreign matter/defect, inspection region, inspection conditions, and the like, among the detection signals (electric signals) obtained from a plurality of photo detectors.

According to this embodiment, an inspection method and inspection apparatus can be provided, which allows for the inspection of an edge region by suppressing the sensitivity reduction in the edge region of an object to be inspected.

The embodiment will be further described with reference to the accompanying drawings. FIG. 1 is a conceptual diagram showing a semiconductor wafer as an object to be inspected and the intensity of diffracted light from an edge region of the wafer, wherein FIG. 1A shows a top view of the diffracted light at an edge region of the wafer, FIG. 1B shows a side view of the diffracted light at the edge region of the wafer, and FIG. 1C shows a state of the scattered light from a foreign matter, respectively.

Figure 1B:
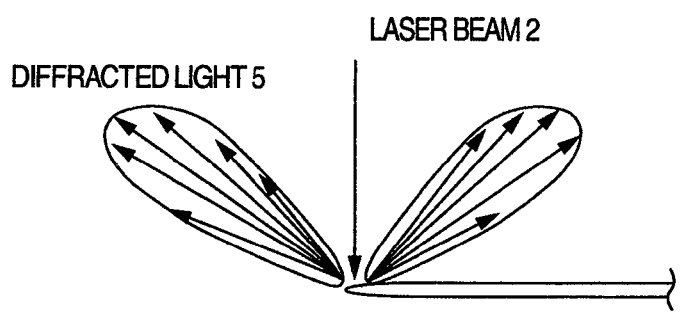
Figure 1C:
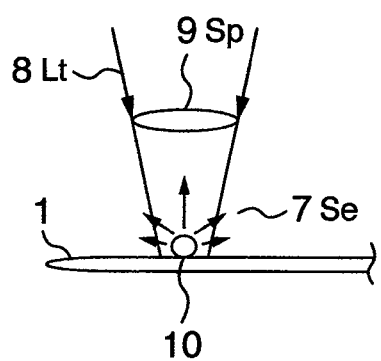

As shown in FIG. 1A, a laser beam 2 is irradiated onto the surface of a wafer 1 with a radius of r 3. When a wafer edge portion, which is an edge region 4 of the wafer 1, is irradiated with the laser beam 2, a strong diffracted light 5 is generated in the diameter direction of the wafer 1. In the tangential direction of the wafer, a weak (small) diffracted light 6 is generated. Because the position of irradiation light is controlled constant and the wafer 1 linearly moves in an approximately constant direction while rotating in the direction shown by the arrow, this strong diffracted light 5 is always present in the diameter direction of the wafer 1. Accordingly, this strong diffracted light 5 will be always in the same direction with respect to a photo detector described below. A scattered light Se 7 from a micro particle, which is the foreign matter, will be buried due to the influence of this diffracted light 5 and thus a desired detection signal can not be obtained. As shown in FIG. 1B, when viewed from the side of the diffracted light at the edge region of the wafer, the laser beam 2 produces the strong diffracted light at the wafer edge, which is the edge region 4 of the wafer 1. As shown in FIG. 1C, when a laser beam Lt 8 is irradiated to the wafer through a laser spot Sp 9 and a foreign matter 10 is present on the surface of the wafer 1, the scattered light Se 7 generates in a wide range of angles (directions) due to the foreign matter 10. When the position to which the laser spot Sp 9 is irradiated is the edge region 4, as described above, the scattered light Se 7 from the foreign matter 10 will be buried due to the influence of the diffracted light and thus a desired detection signal can not be obtained. In the following, an inspection method and inspection apparatus capable of dissolving the above-described problem will be described.

Figure 2A:
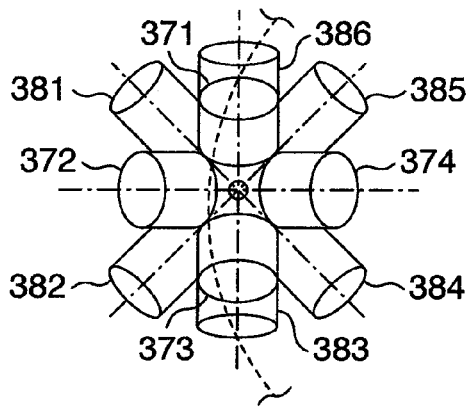
Figure 2C:
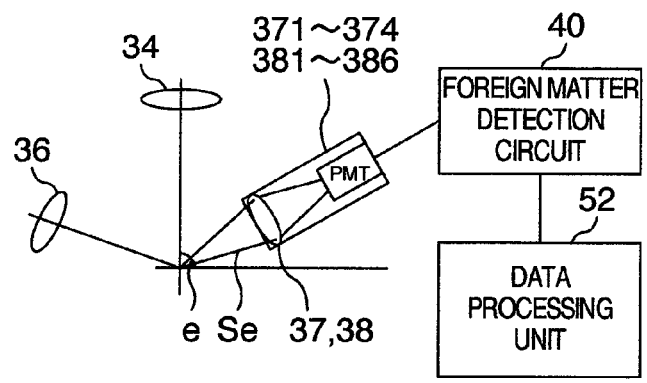
Figure 2B:
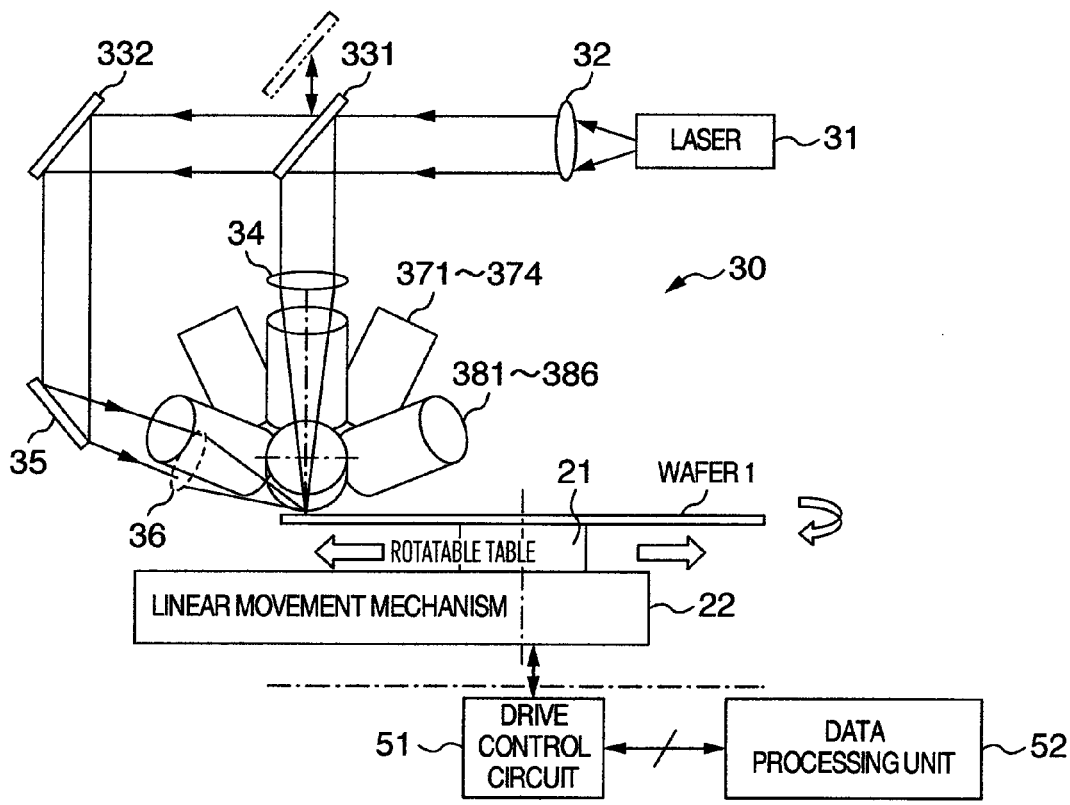

FIG. 2 is a simple configuration diagram of a detection optical system of the inspection apparatus, wherein FIG. 2A shows a top view of the arrangement of photo detectors, FIG. 2B shows a simple side view of the configuration of the optical system, and FIG. 2C shows a detailed diagram of the photo detector, respectively.

The configuration of the wafer surface inspection apparatus is described using FIG. 2. As shown in FIG. 2B, the surface inspection apparatus comprises a rotatable table 21, a linear movement mechanism 22, an inspection optical system 30, a data processing unit 52, and the like. The wafer 1, which is an object for the inspection, is placed on the rotatable table 21. The inspection optical system 30 disposed above this wafer 1 includes a laser beam source 31 provided with a laser oscillator. The laser beam Lt outputted therefrom is made parallel via a collimating lens 32 and is reflected by a mirror 331 in a first light projecting optical system, and is then projected approximately perpendicularly onto the surface of the wafer 1 as a laser spot Sp (hereinafter, referred to as a spot Sp) that is focused by a condenser lens 34, (perpendicular irradiation). Moreover, in a second light projecting optical system, the mirror 331 is moved away from the optical path of the laser beam Lt and thus the laser beam Lt is reflected by a mirror 332 and a mirror 35, and is projected obliquely onto the surface of the wafer 1 as the laser spot Sp 9 (hereinafter, referred to as the spot Sp) that is focused with a condenser lens 36, (oblique irradiation). The laser spot Sp 9 perpendicularly irradiated or obliquely irradiated scans the wafer in response to the movement of the wafer 1. The wafer 1 is rotated by the rotatable table 21 and the linear movement mechanism 22 and at the same time is moved in the radial direction (X direction: the arrow direction in the view) corresponding to the rotational speed. Thereby, the spot Sp scans the surface of the wafer 1 in a spiral manner so that the entire surface of the wafer 1 is scanned. In addition, the driving of the rotatable table 21 and linear movement mechanism 22 is controlled via a drive control circuit 51 by the data processing unit 52.

As described above, when the foreign matter 10 is present on the surface of the wafer 1 as shown in FIG. 1C, the spot Sp 9 produces the scattered light Se 7 in a wide range of angles (directions) due to the foreign matter 10. As shown in FIG. 2C, a part thereof is condensed by a condenser lens 37 or 38 and is received by photomultiplier tubes (hereinafter, referred to as PMT) 371-386 serving as photoelectric converters. The light incident upon PMTs 371-386 is converted here into an electric signal and the converted electric signal (received light signal) is inputted to a foreign matter detection circuit 40. The foreign matter detection circuit 40 compares the received light signal with a predetermined threshold value $V_{TH}$ using a single-ended differential amplifier and amplifies the component exceeding the threshold value $V_{TH}$. Accordingly, the detection signal whose noise component is removed is inputted to the data processing unit 52.

The detection signal is once stored in a memory (not shown) using an A/D conversion circuit (A/D) (not shown) provided in the data processing unit 52, and then a processing unit (MPU) (not shown) executes a predetermined program to thereby data process the detected data along with the data of the concerned scanning position (detection position). As a result, the size of the foreign matter 10 is determined depending on the detection value. Moreover, the number of foreign matters is counted. Moreover, through execution of the predetermined program by the MPU, data of the foreign matter indicative of the number, size, and position of the foreign matter 10 is generated and outputted such as to a printer (not shown) and a display (not shown) for displaying the conditions of the foreign matter in a map form.

FIG. 2A shows an example of the arrangement as seen from above the photomultiplier tubes (PMT) 371-386. FIG. 2B shows an example of the arrangement as seen from the side of PMTs 371-386. This inspection apparatus includes a light receiving optical system consisting of two groups, wherein as seen from the beam spot above the wafer, the arrangement is made such that the elevation angle of a group of PMTs 371-374 with respect to the wafer plane is higher (greater) than the elevation angle (with reference to the wafer surface) of a group of PMTs 381-386. Then, PMTs 371-374 are referred to as high angle photo detectors. Moreover, PMTs 381-386 are referred to as low angle photo detectors. From a viewpoint that the scattered light from a defect seldom enters but the scattered light from a sticking foreign matter can be mainly received, it is preferable that the elevation angle of the low angle photo detector is set to approximately 30 degrees or less with reference to the wafer surface, desirably in a range of 5 to 20 degrees. From a viewpoint that the scattered light from a defect can be received strongly, it is preferable that the elevation angle of the high angle photo detector is set to approximately 30 degrees or more with reference to the wafer surface, desirably in a range of 35 to 65 degrees. Using a combination of the light projecting optical system and the light receiving optical system, it is possible to discriminate between these foreign matter and defect with higher accuracy. In the detection of foreign matters, a combination of the oblique irradiation, which uses the second light projecting optical system, and the low angle photo detector is preferable. Moreover, in the detection of defects, it is preferable that the light receiving optical system is set to the high angle photo detector, and that a combination with the first light projecting optical system or the second light projecting optical system is selected depending on the type of the defects of the wafer 1 to be identified. Moreover, by means of a mirror switching mechanism (the drawing is omitted) for switching from the mirror 331 to a half mirror, beams from the first light projecting optical system and from the second light projecting optical system are simultaneously irradiated, and the scattered light from the wafer 1 is detected with the low angle photo detector and the high angle photo detector, so that the discrimination between foreign matters and defects, and a high-speed inspection can be made.

In addition, as seen from the above, in the group of six PMTs 381-386, each PMT is disposed at an angle of approximately 60 degrees. In the group of four PMTs 371-374, each PMT is disposed at an angle of approximately 90 degrees. Then, PMTs 372 and 374 are disposed in the diameter direction (the direction in which the strong diffracted light is produced) of the wafer, which is an object for the inspection, and also on the same line or on the parallel lines as seen from the above.

As shown as an example in FIG. 2, there is provided a wafer surface inspection apparatus including: the low angle light receiving system having an elevation angle equal to or less than 30 degrees with reference to the surface of the wafer; the high angle light receiving system having an elevation angle greater than that of the low angle light receiving system; the first light projecting optical system that irradiates a laser beam approximately perpendicularly from above the wafer, and the second light projecting optical system that irradiates a polarized laser beam from the oblique direction of the wafer, wherein defects and sticking foreign matters are discriminated by computing the signals that the low light receiving system and the high angle light receiving system detect via the irradiation of a laser beam from the first light projecting optical system, and sticking foreign matters are identified based on a signal that the low angle light receiving system detects via the irradiation of a polarized laser beam from the second light projecting optical system. This wafer surface inspection apparatus further includes the optical system switching mechanism that switches between scanning with the laser beam of the first light projecting optical system and scanning with the second light projecting optical system and can display the detected defect or sticking foreign matter in a map form on a screen of a display.

Before the scanning with a laser beam enters into an edge region of the wafer, which is an object for the inspection, the photo detectors (photomultiplier tubes 371, 373, 383 and 386) with an angle not receiving the diffracted light (or less influenced by the diffracted light) are selected, and based on the signals of the selected photo detectors the measurement is carried out, and thereby the signals of a foreign matter, defect, or the like, can be obtained without being influenced by noise due to the diffracted light from the edge region (or, the influence can be reduced). Moreover, a position sensor (not shown) is provided in the wafer scanning mechanism in order to recognize the range of the edge region, and based on a signal from this position sensor, and based on the size information on the semiconductor wafer, which is an object for the inspection, the size information being inputted in advance or obtained via the optical sensors, the data processing unit 52 determines that the beam spot is present in the vicinity of an edge region (or is approaching thereto). Subsequently, the operation (function) of a predetermined photo detector or the operation (function) of a photo detector, which is determined to be stopped by the data processing unit 52, is stopped. Alternatively, the acquisition of the signal from the above-described photo detector may be stopped. As the position sensor, an encoder (not shown) provided in a driving motor that is incorporated into the linear movement mechanism 22 may be used. Moreover, the wafer may be imaged optically and the image may be analyzed with a known analysis technique to thereby calculate the position of the wafer or the position of the beam spot. For example, in the case where the beam spot position is fixed, whether it is at the edge region or not is determined based on the position of the wafer.

In case of inspecting only the edge region, the measurement start position is set to a position short of the edge region and the photo detector is selected so as not to receive the noise component, thereby allowing for the measurement of only the edge region. Then, used in combination with the inspection (measurement) of other than the edge region, the inspection (measurement) of the whole wafer can be made. As an example of the method of selecting a photo detector, a photo detector in the direction into which a noise component enters is desirably turned off in order to avoid an excess input thereto. Alternatively, the sensitivity of this photo detector may be reduced.

Figure 3:
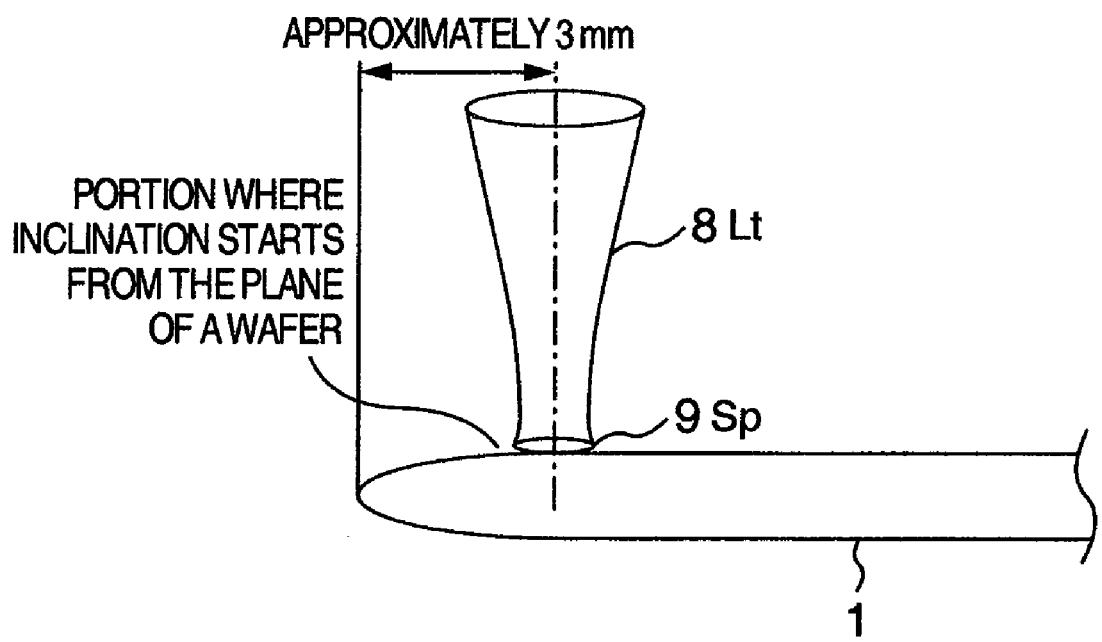
FIG. 3 is an explanatory view of an edge region in an embodiment of the present invention.

The definition of a wafer edge region is described using FIG. 3. When the edge portion of the laser spot Sp 9 of the laser beam Lt 8 that is irradiated to the wafer 1 comes to a portion where an inclination starts from the plane of the wafer, the diffracted light becomes strong and starts to influence the detection. The range from a portion, where the diffracted light becomes strong in this manner, to the wafer edge is defined as the wafer edge region. As shown in FIG. 3, in case of the edge region of a wafer, it is preferable that the region from the wafer 1 radius from r minus approximately 3 mm to the wafer radius r mm is assumed to be the wafer edge region.

In this embodiment, in the method including the steps of: emitting a laser beam onto the wafer surface; and rotating the wafer and thereby inspecting micro particles on the surface of the wafer, it is desirable to detect a micro particle, which is the foreign matter, using a photo detector upon which the diffracted light is not incident as much as possible, so as to minimize the sensitivity reduction in the edge region (wafer radius r minus approximately 3 mm) of the wafer 1.

In the above-described embodiment, also in the method including the steps of: emitting a laser beam onto the wafer surface; and rotating the wafer and thereby inspecting, it is desirable to dispose photo detectors in portions except at the angle of receiving the diffracted light because the direction of the diffracted light from the known wafer edge region is always approximately the same with respect to the rotation. In the above-described embodiment, the measurement (inspection) is carried out by selecting the photomultiplier tubes 371, 373, 383 and 386 so that the photo detectors may not receive the strong diffracted light 5 shown in FIG. 1A. Moreover, the number and arrangement of the photo detectors may be set suitably so as to avoid the strong diffracted light 5.

It is also desirable to include the light projecting optical system that irradiates the laser beam approximately perpendicularly from above the wafer, and further to include a means that selects a photo detector with an angle less likely to be influenced by the diffracted light, in combination of the photo detectors. It is also desirable to include the light projecting optical system that irradiates the laser beam from the oblique direction of the wafer, and further to include a means that selects a photo detector with an angle less likely to be influenced by the diffracted light, in combination of the photo detectors. It is also desirable to include the photoelectric converter, and to dispose a photo detector also at an angle not influenced by the diffracted light from the wafer edge region, thereby allowing for the selection. In order to realize these, it is desirable to include the scanning mechanism that scans the wafer with a laser beam, the scanning mechanism consisting of the rotating stage 21 and the straight line stage 22, and the data processing unit that receives the detection signal from the photoelectric converter (PMT) to thereby detect a micro particle.

As described above, for example, in the conventional wafer surface inspection apparatus, due to the diffracted light by the edge region of a wafer, the outer periphery portion of the wafer is set to a region not to be inspected (non-inspection region), thus making it difficult to inspect foreign matters. Moreover, even if attempting to set the outer periphery portion of the wafer to the inspection region, a photo detector may be damaged by the diffracted light. For this reason, a critical defect of the wafer might have been overlooked. For the purpose of improving this, when measuring the edge region, photo detectors with an angle not influenced by the diffracted light, the diffracted light causing noise, are selected, thereby allow for inspection that minimizes the sensitivity reduction. By employing the above-described solving means, foreign matters in the outer peripheral portion, which conventionally could not be measured or was difficult to be measured, can be managed, and the oversight of critical defects on the wafer can be eliminated, and the reduction of failures of IC can be attained. In order to reduce the above-described noise component, the amount of received light is varied, but other example include the step of varying the amount of irradiated light, e.g., minimizing the output of a light source, or a dimming means, such as a filter, may be included in the middle of the irradiation system. The embodiment of the present invention has been described above, but it is apparent that various modifications can be contemplated without departing from the spirit and scope of the present invention.

As described above, the present invention is intended to solve the problems at the time of inspecting an object to be inspected, the object having a specified region such as an edge region, and can be used for not only semiconductor wafers but wafer-shaped objects, insulator wafers, and the like.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus, comprising:
    a scanning system which moves a substrate;
    a first irradiating unit which irradiates said substrate with approximately perpendicular light;
    a second irradiating unit which irradiates said substrate with oblique light;
    a position sensor which detects a first position of said perpendicular light on said substrate and detects a second position of said oblique light on said substrate, said position sensor being provided on said scanning system;
    a detecting system which detects a light from said substrate, said detecting system including a first high angle detecting unit, a second high angle detecting unit, a first low angle detecting unit and a second low angle detecting unit; and
    a first processing unit which inspects said substrate responsive to detected light, wherein:
    said first processing unit classifies a defect and foreign matter by using a combination of:
        at least one of said first irradiating unit and said second irradiating unit, and
        at least one of said first high angle detecting unit, said second high angle detecting Unit, said first low angle detecting unit and said second low angle detecting unit;
    said first high angle detecting unit and said first low angle detecting unit are arranged to detect light propagating substantially in a tangential direction relative to said substrate, the tangential direction corresponding to a direction of diffraction light having weaker intensity than another light propagating in a direction different from the tangential direction; and
    said first high angle detecting unit and said first low angle detecting unit operate according to said first and second positions detected by said position sensor.

2. An inspection apparatus according to claim 1, further comprising a second processing unit which selects said combination, corresponding to kind of defects.

3. An inspection apparatus according to claim 1, wherein said oblique light is polarized laser.

4. An inspection apparatus according to claim 1, wherein said first irradiating unit and said second irradiating unit irradiate light at the same time.

5. An inspection apparatus according to claim 1, wherein an edge region is recognized based on a signal from said position sensor and size information on said substrate, and then operation of said detecting system is determined.

* * * * *